United States Patent [19]

Grow

[11] 4,411,989

[45] Oct. 25, 1983

[54] PROCESSES AND DEVICES FOR DETECTION OF SUBSTANCES SUCH AS ENZYME INHIBITORS

[75] Inventor: Ann E. Grow, Kansas City, Mo.

[73] Assignee: Midwest Research Institute, Kansas City, Mo.

[21] Appl. No.: 292,611

[22] Filed: Aug. 13, 1981

[51] Int. Cl.$^3$ .......................... C12N 9/12; C12N 9/18; C12N 9/76; C12N 11/00; C12Q 1/46; C12Q 1/48; C12Q 1/38; C12M 1/34

[52] U.S. Cl. .......................................... 435/20; 435/15; 435/23; 435/174; 435/199; 435/197; 435/213; 435/291; 435/807; 435/4

[58] Field of Search ...................... 435/15, 20, 23, 288, 435/291, 313, 174, 807, 808, 289, 4, 194, 197, 213

[56] References Cited

U.S. PATENT DOCUMENTS

| | | | |
|---|---|---|---|
| 3,049,411 | 8/1962 | Gelman et al. | 435/20 |
| 3,081,158 | 3/1963 | Winter | 435/20 |
| 3,378,463 | 4/1968 | Guilbault et al. | 435/20 |
| 3,451,901 | 6/1969 | Seiger et al. | 435/20 |
| 3,515,644 | 6/1970 | Kramer et al. | 435/20 |
| 3,526,480 | 9/1970 | Findl et al. | 422/66 |
| 3,539,452 | 11/1970 | Penicnak | 435/20 |
| 3,689,224 | 9/1972 | Agnew et al. | 435/20 |
| 3,715,298 | 2/1973 | Goodson et al. | 435/20 |
| 3,730,841 | 5/1973 | Salvatore et al. | 435/182 |
| 3,741,876 | 6/1973 | Guilbault et al. | 435/20 |
| 3,809,616 | 5/1974 | Schmitt et al. | 435/20 |
| 3,912,704 | 10/1975 | Singh | 435/23 |
| 4,059,491 | 11/1977 | Iwasa et al. | 23/230 B |
| 4,324,858 | 4/1982 | Goodson et al. | 435/20 |

OTHER PUBLICATIONS

Makinen et al., *Ann. Rev. Biophys. Bioeng.* 6:301 (1977), pp. 301-343.

*Primary Examiner*—Esther M. Kepplinger
*Attorney, Agent, or Firm*—Connolly and Hutz

[57] ABSTRACT

The disclosed methods and devices for detecting or monitoring or identifying substances (such as chemical warfare agents) and residual environmental pollutants (such as pesticides) utilize the discovery that spectra (e.g. infrared absorption spectra) of an uninhibited enzyme (e.g., a cholinesterase) can differ from spectra of the same enzyme which has been complexed with the agent pollutant. For example, the infrared spectrum of uninhibited butyrylcholinesterase (BuChE) lacks a distinct absorption peak found at about 1000 cm$^{-1}$ in the BuChE-Malathion spectrum. The enzyme is used to collect and concentrate the agent or pollutant, and the resulting complexed enzyme can then be analyzed (e.g., by infrared spectroscopy) and its spectrum compared to an uninhibited enzyme spectrum.

Relatively simple devices can carry out the collection and detection or monitoring or identification steps of this invention, given appropriate models of complexed and uncomplexed enzyme specta upon which to base the design of the devices.

9 Claims, 2 Drawing Figures

PROCESSES AND DEVICES FOR DETECTION OF SUBSTANCES SUCH AS ENZYME INHIBITORS

TECHNICAL FIELD

This invention relates to a method and a device for detecting the presence of enzyme inhibitors in a fluid medium such as air or water. An aspect of this invention related to the detection of nerve agents (such as Tabun, Sarin, Soman, VX, etc.), various other toxic agents (such as cyanide), environmental pollutants, and other substances capable of inhibiting the enzymatic activity of enzymes such as the cholinesterases, hexokinase, and the like. Still another aspect of this invention relates to the collection and specific identification of such substances in the atmosphere or other areas of the environment such as water supplies. A still further aspect of the invention relates to instrumentation for implementing the aforementioned methods including point source alarms, dosage monitors, and detection/identification systems.

DESCRIPTION OF THE PRIOR ART

It is well known that enzymes such as the cholinesterases are useful in methods and devices for detecting the presence of nerve agents, pesticides, and other toxic substances. The cholinesterases and similar enzymes are inhibited by these substances; hence tests for enzyme activity (or the lack of enzyme activity) can reveal the presence of the toxic substance. For example, a layer of a cholinesterase can be exposed to a sample of surface water (from a lake, stream, or other body of water), or an aqueous solution through which air has been bubbled, and the activity of the thus-exposed cholinesterase can be measured chemically, biochemically, or with an electrical or electronic instrument. A lack of activity indicates that the cholinesterase has been inhibited by a substance in the sample of air or water to which the enzyme layer was exposed.

Typically, the concentration of toxic substances or agents in the air or water supplies is small, but even very small concentrations can be brought within the range of sensitivity of prior art methods. One known means for insuring high sensitivity involves collecting trace quantities of the agent upon or in a sensitive collection medium thereby increasing the concentration of agent for detection or monitoring purposes. Various adsorbents (e.g., "TENAX," "PORAPAK Q," and activated charcoal) collect agents satisfactorily when sampling clean air. However, when these adsorbents are used in an outdoor environment, they collect other airborne substances which may mask the presence of specific agents.

To improve both sensitivity and specificity of detection, immobilized cholinesterase has been used to collect as well as detect agents such as dimethyl-2, 2-dichlorovinyl phosphate (DDVP) at concentrations as low as 0.4 mg/m$^3$ when the sampled air volume is 2 liters. See A. W. Barendsz, *Intern. J. Environ. Anal. Chem.* 6:89 (1979), wherein there is disclosed a detection tube containing an indicator layer and butyrylcholinesterase immobilized in a gelatine preparation. The sealed glass ends of the detection tube can be broken off and a volume of air (e.g., 2000 cm$^3$) pumped through the tube. Observation of a strong blue color change indicates no change in enzyme activity, i.e., that no agent was collected—or that the amount of agent collected was below the lowest level of sensitivity of the test method. But if the air sample has inhibited the butyrylcholinesterase due to collection of enzyme inhibitors in the gelatine preparation, the deep blue hydrolysis product will not be observed in the indicator layer.

The foregoing prior art method is believed to be specific for cholinesterase inhibitors (anticholinesterases) and some very closely related compounds—a fairly narrow class of agents. However, it is believed to be difficult to ascertain by this method which of the anticholinesterases has been detected. That is, it is particularly desirable to have a relatively simple method and device which is specific as to the class or classes agents which it collects and concentrates and which is capable of being specific in its detection or monitoring responses, even within the bounds of the class which has been collected. Such a method or device would have two levels of selectivity: it would screen out all compounds except certain enzyme inhibitors or substrates in the collection stage, and it would provide further specificity in the detection or monitoring stage, thereby identifying the agent which has been collected.

SUMMARY OF THE INVENTION

It has now been found that analytical techniques based upon the emission and subsequent measurement or detection of wave energy (e.g., infrared radiation) can be used to detect the presence of enzyme inhibitors such as the anticholinesterases, and, if desired, to identify the specific inhibitor which has been detected. The adaptation of these analytical techniques to the field of detecting and/or monitoring and/or identifying the inhibitor is based in part upon the discovery that one or more readily detected or measured characteristics (e.g., the infrared absorption) of the enzyme (e.g., a cholinesterase, hexokinase, or other enzyme sensitive to toxic agents or the like) are significantly altered after the enzyme has been used to collect the agent to be detected.

Although this invention is not bound by any theory, it is believed that the agents of concern in the context of this invention form a third substance (which can be referred to as EnzInhib), distinct from both the enzyme and the agent, which has its own identifiable characteristics, e.g., a distinctive infrared adsorption spectrum whether the enzyme is in solution or in a dry state when exposed to the inhibitor. It is by no means universally accepted in the art of analytical chemistry that alterations in the structure of both the enzyme and the inhibitor occur when dry enzyme and inhibitor come together or that the two form a complex with a new chemical bond. Studies done in connection with this invention suggest that such structural alterations probably do occur, however. Additional data, although not as extensive, suggest that the complex is inhibited enzyme. Prior art workers have studied the infrared spectra of various uninhibited enzymes and various substrates or inhibitors, but spectral data on solubilized enzyme-inhibitor combinations appear to be relatively scarce. Spectra of dry enzymes, without or with inhibitor, have apparently not been reported. It has now been found that, using the uncomplexed or uninhibited enzyme spectrum as basis for comparison, dramatic spectral changes can occur after collection of the inhibitor with the enzyme, particularly when the inhibitor is a chemical warfare agent or an organophosphorous pesticide. This phenomenon can be qualitatively detected and—to some extent—quantitatively measured with known infrared spectroscopic techniques. When comparing absorption spectra ("inhibited" vs. "uninhibited" enzyme), it has beed found that absorption peaks can be shifted, reduced in intensity, or even substantially eliminated. Furthermore, new absorption peaks may appear in the "inhibited" spectrum which were not present in the "uninhibited" spectrum.

Again, this invention is not bound by any theory, but the foregoing spectra comparisons are believed to support the concept that the inhibitor (e.g., a nerve agent) gets tied into the enzyme structure in some manner, resulting in losses or changes in chemical substituents or functionality of the inhibitor and/or the enzyme. Theoretically, then, the complex EnzInhib is a unique chemical species, differing identifiably from both of its parent compounds or precursors. Even if this theory is not correct, the aforementioned changes in the spectra are sufficiently dramatic to insure the practicality of this invention. Not only do these spectral changes reveal that an inhibitor has been collected by the enzyme, they also tend to identify the specific inhibitor, since different inhibitors appear to cause different spectral shifts with respect to the same enzyme. Mixtures of inhibitors can, if desired, be sorted out and separately identified.

Briefly, then, the method of this invention, which enables one to detect the presence of one or more given enzyme inhibitors in a fluid medium, comprises the steps of:

(a) collecting a portion of the inhibitor in the fluid medium by bringing the fluid medium into contact with substantially uncomplexed or uninhibited enzyme (the uncomplexed enzyme being preferably in a dry, immobilized state), thereby forming an enzyme-inhibitor combination, and (b) detecting any wave-energy interaction characteristic of the enzyme-inhibitor combination at a given wavelength which is different from the wave-energy interaction characteristic of the substantially uncomplexed or uninhibited enzyme at that same wavelength.

Preferably, the wave energy is infrared energy, and the most conveniently detected interaction with this energy is absorption or transmission, which can be measured with conventional infrared spectrometers or with multiple internal reflection (MIR) infrared spectroscopy. The fluid medium can be air, water, solvents, carrier gases, etc. and the results obtained with the method can be annunciated with an alarm sound or light, a digital readout, a print-out, a continuous plot on graph paper, an analog signal on an electronic display, or other electrical or electronic or acoustic or hard-copy forms of display or annunciation. Controlled studies can generate the baseline data for comparing the infrared absorption characteristics of the enzyme-inhibitor combination with the substantially free or uninhibited or uncomplexed enzyme and also suggest specific wavelengths or frequencies which will provide a particularly definitive determination of the presence of a given inhibitor or agent.

Devices useful in this invention can either be fully integrated (with collection or sampling means and sample identification or detection equipment all combined in one unit) or can consist essentially of sample identification equipment constructed and arranged to receive a sample collected with a separate unit such as an exposure badge or water-sampling kit.

DETAILED DESCRIPTION

Figure 1:
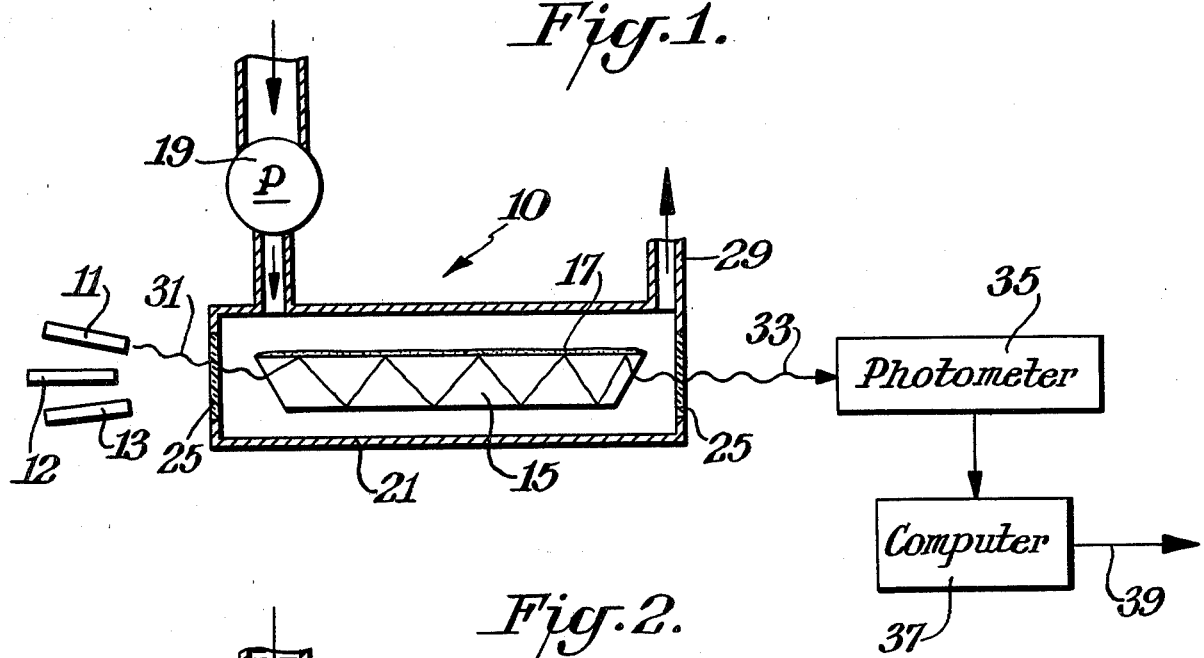
FIG. 1 is a schematic representation of an infrared identification device of this invention.

While this invention can be used to detect the presence of pollutants (herbicides, pesticides, etc.) and a wide variety of non-military toxic substances through selection of appropriate enzyme collectors, the following description will, for the sake of brevity, focus on chemical warfare agents such as GB (Sarin), GD (Soman), VX, L, BZ, Tabun, mustard gases, and organophosphorus compounds which complex with cholinesterases. The principles of this invention are easily adapted to industrial and other non-military applications. Known enzymes can collect or complex with pollutants or toxic substances having no substantial military use.

In detecting or monitoring for the presence of nerve agents, the normally preferred class of enzymes is the cholinesterases. The toxicity of nerve agents stems from their ability to irreversibly inhibit this type of enzyme, which is necessary for the proper functioning of the nervous system. Once the agent has inhibited the enzyme, it rapidly undergoes hydrolysis, a process known as "aging," which makes reactivation of the enzyme impossible; the enzyme-agent complex is chemically the same compound after aging whether the agent (inhibitor or anticholinesterase) was GA, GB, GD, or VX. It might be expected, therefore, that identification of the inhibitor would not be possible. It has been found, however, that such identification can be possible when airborne anticholinesterases are collected with dry, immobilized cholinesterase. Apparently, the "aging" process is substantially slowed so that an identifiable moiety of the anticholinesterase maintains its unique composition or structure indefinitely when kept relatively dry. Accordingly, from the standpoint of accuracy of identification, dry cholinesterase is the preferred collecting matrix. Cholinesterase is readily immobilized by fairly simple techniques, e.g., adsorption on filter paper. Gels have also been used for immobilization. Immobilization is not absolutely essential for sampling air, however. For example, dry crystalline cholinesterase can be packed in a tube with fibrous plugs at each end, and air can be pumped through the tube.

If a high degree of specificity is desired for identification of water-borne agents, the enzyme can be entrapped or convalently bound to or absorbed on surfaces to be used to collect nerve agents in water. In the context of this invention, it has been determined that immobilization by covalent binding of cholinesterase tends to slow the "aging" process significantly, and some specificity of identification is possible even in water solution. Chymotrypsin, another enzyme which is inhibited by nerve agents, is reported to be resistant to "aging" and thus presents an alternative to cholinesterase for identification of water-borne agents.

There is a controversy in the literature as to whether vesicants such as mustard gas are cholinesterase inhibitors. In an embodiment of the enzyme collection/infrared spectra comparison technique of this invention (using crystalline acetyl cholinesterase from eels) only minor differences in the spectra were observed. Accordingly, better detection of mustard gas can be obtained with a different enzyme or enzyme preparation. On the other hand, eel, bovine, and horse serum acetyl cholinesterase were all found not only to be effective in detecting nerve agents (GB, GD, etc.) an organophosphorous agents (including "Malathion," "Fonofos," and "Dichlorvos") but also in distinguishing these various agents from each other. Devices for the detection of nerve agents and blistering agents may have mixtures of enzymes or separate ports or windows, i.e., a window for each enzyme. In the case of a detection or monitoring device exposed to both nerve agents and organophosphorous pesticides, separate enzyme collectors are ordinarily not necessary, since the characteristic shifts or new peaks or reduced intensity peaks in the cholinesterase-nerve agent spectra are somewhat different in frequency and generally non-interfering with respect to the characteristic bands of the cholinesterase pesticide spectra. This lack of interference between two closely related classes of cholinesterase inhibitors is considered a highly advantageous feature of this invention.

Presently available data also indicate that uncontrolled exposure to the atmosphere in an urban environment (which presumably contains a variety of airborne pollutants) does not interfere with nerve agent detection and identification, even if no attempt is made to flush off the nonspecifically adsorbed pollutants. In short, the present invention appears to have a capability for detecting or monitoring or identifying specific individual agents, specific classes of agents, or selected groups of individual agents or classes of agents. Given the teachings of this invention, it is within the skill of the art to select the particular enzyme or groups of enzymes to be used as collectors (e.g., one or more cholinesterases, chymotrypsin, hexokinase, an combinations of these enzymes).

Commercially available crystalline acetyl cholinesterases (AChE) perform well in detectors and monitors made according to this invention, as do the so-called pseudo-cholinesterases (BuChE) obtainable from horse serum or human serum.

Acetyl cholinesterase occurs as a membrane-bound enzyme and is obtained in commercial quantities from electric eels or bovine erythrocytes. The base line spectra (uninhibited or uncomplexed enzyme spectra) of, for example, eel, bovine, and horse serum cholinesterases differ markedly from each other, but each base line shows significant shifts or changes after collection of a nerve agent or organophosphorous pesticide. Indeed, the differences between the cholinesterases in base line spectral data can be put to good use; BuChE may be the enzyme of choice for one agent, and AChE for another.

DETECTION, MONITORING, AND IDENTIFICATION DEVICES

For convenience of description, it will be assumed that the devices discussed below are designed to detect and/or monitor and/or identify nerve agents or organophosphorous pesticides. It will also be assumed that detection (e.g., determining the presence or absence of an agent in a fluid sample), monitoring (e.g., use of real-time monitors for demilitarization plants, personnel exposure badges, etc.), and identification (determining which particular nerve agent or pesticide has been detected or monitored) will all be accomplished through collection by an enzyme (preferably a cholinesterase) and infrared analysis of the resulting enzyme-agent or enzyme-pesticide complex. Because of the relatively well-defined widths and locations of many of the infrared absorption bands of interest, the infrared analysis of the Enz-Inhib complex may be confined to a single wavelength or wave number, narrow band of wavenumbers, or a few wavelengths or bands of wavenumbers. For example, if the agent to be detected is GB, and the GB is collected and concentrated on a layer of immobilized bovine erythrocyte acetyl cholinesterase (AChE), a reasonably sharp absorption peak for the AChE-GB complex should be observed at about 13.8 micrometers, i.e. 725 reciprocal centimeters ($cm^{-1}$), which peak is substantially nonexistent in the uninhibited bovine erythrocyte AChE spectrum.

Thus, to analyze samples for AChE-GB, where the AChE is from bovine erythrocytes, the infrared source can be optically narrowed to 700–750 $cm^{-1}$, and the determination of percent transmission of the focused 700–750 $cm^{-1}$ beam can be made with respect to an attenuated reference adjusted to the equivalent of about 65% transmission. The reference will be less transmissive than an uninhibited bovine AChE sample; hence an AChE sample which has collected no GB will be "seen" as lacking an absorption band at the selected range of wavelengths. An absorption peak at approximately the same wavenumber i.e., 725 $cm^{-1}$ appears to indicate the AChE-GD complex as well as AChE-GB. In cases where both agents may be expected to be present, a second wavenumber, e.g., 950 $cm^{-1}$, may also be monitored. There is strong absorption in uncomplexed enzyme and in AChE-GB at this wavelength, but a substantial decrease in absorption for the AChE-GD complex. Thus an increase in absorption at 725 $cm^{-1}$ with no change at 950 $cm^{-1}$ would be "seen" as AChE-GB, while an increase at 725 $cm^{-1}$ and a decrease at 950 $cm^{-1}$ would be "seen" as AChE-GD. Substantially similar arrangements can be made for detecting AChE-GD and AChE-GB when the acetyl cholinesterase is obtained from electric eel sources.

In the case of Malathion, the BuChE-Malathion spectrum has a characteristic absorption peak at about 1000 $cm^{-1}$ (about 10 micrometers) which does not appear in the uninhibited BuChE spectrum. Thus, Malathion can be detected, monitored, and identified in a manner analogous to the nerve agents.

In any case, the output of the spectrophotometric cell can be converted to either a digital or analog signal which can be compared in numerical value or in intensity to a reference signal. The differential output from the comparison means can be fed to a digital display, alarm means, print-out device, or the like. The area of a peak can be integrated by computer and compared to the area of reference peaks by known techniques.

As noted previously, immobilized "dry" enzymes are particularly preferred for collecting and concentrating the agents to be detected and/or identified. The "dry" enzymes are not necessarily bone dry; oftentimes, perfect dryness is impractical because the preferred enzymes are hygroscopic proteins. However, it is neither necessary nor desirable for macroscopic amounts of water to be present, particularly when the fluid samples to be analyzed for agents are gaseous (e.g. air). When aqueous samples are analyzed, wetting of the enzyme can be and preferably is minimized, as explained in the discussion regarding FIG. 2 of the drawing. Typical dry enzymes used in detection elements of this invention have at least the appearance of substantially dry crystals, and the mechanism by which the crystalline enzyme interacts with fluid-borne agents (e.g. in air samples) is not fully understood.

By means of multiple internal reflection (MIR) infrared spectrophotometry, absorption spectra can be obtained for both dry, uncomplexed enzyme and the dry complex Enz-Inhib. In one embodiment of this invention, reliable model spectra—or portions of spectra—are obtained in advance and stored (e.g. in digital form) in a computer memory to provide a basis for comparison and/or to provide an internal standard or baseline. If desired, a model spectrum can be obtained at a given time (e.g. in the morning) from the dry immobilized cholinesterase layer on a dosimeter badge. When stored in a computer memory, this model can then be compared to the vary same cholinesterase layer after several hours of exposure, e.g. in the early evening of the same day that the "model" was obtained.

Reference or model spectra or baselines for comparison can also be obtained simultaneously with analysis of an exposed dosimeter or air sample by techniques such as beam splitting (using a commom broad- or narrow-spectrum infrared energy source), attenutation of reference beams, passing the reference beam through an uncomplexed dry enzyme "blank", and the like. When air is being sampled directly (e.g. with a real-time air monitor or alarm device), an air pump is normally used so that the volume of air passing over the detection element (which can contain a layer of dry, immobilized enzyme) in an eight-hour period will be very large. If the infrared energy source is omnidirectional and broad in its spectrum (e.g. a heated black body), specific bands can be selected with a prism or grating, as is known in the art. It is also known in the art that suitably "pumped" crystals (e.g. lasers) can produce narrow-spectrum or even monochromatic infrared radiation, thereby greatly simplifying the optics of the detection system, since in most cases one or two or three very narrow bands will be sufficient for both detection and identification of various agents. As noted previously, as few as two infrared bands can be sufficient to distinguish closely related agents which might otherwise interfere with each other in a single-wavelength analysis. Quantitative measurements (e.g. % absorption) can add the further dimension of roughly estimating a cumulative dose or determining when a dose has gone beyond a previous peak level.

This invention contemplates several different types of infrared analysis devices, the three general types described below being illustrative.

(a) A dosimeter badge "reader", which has an MIR (multiple internal reflection) crystal and a simple computer capable of storing the readings. (The badge includes a layer of dry enzyme immobilized on a flat surface which can be pressed against the MIR crystal.) The computer stores the model spectrum data, typically complete spectra or at least several preselected wavelengths. The stored daily readings can be calibrated against the model data; hence daily and cumulative exposure can be determined for at least one or two and preferably several agents.

(b) A real-time alarm, in which the enzyme for collecting the agent is in an element of the detection device itself, albeit a replaceable element, e.g. a coating on a replaceable transmission window or MIR crystal. Typically the alarm is designed to be triggered by only one or two agents, and a very few narrow bands or even a single band of infrared energy would be sufficient to detect a dangerous rise in nerve agent concentration in the atmosphere. (Sampled ambient air may be heated, cooled, dried, filtered, or the like to optimize sensitivity, and an air pump can be used to provide a large sample.) When the ambient concentration of nerve agent is zero or at a known level, the alarm device can be "zeroed" at the pre-selected wavelength or wavelengths, so that any decrease in percent absorption at a critical wavelength will activate the alarm. A computer, if included in this device at all, could be of the simplest type, e.g. a microprocessor chip.

(c) A detection/identification instrument, which would also include dry enzyme as an element, but with computer capabilities to identify and quantitate agents. An air pump would again be desirable for large air samples.

Turning now to the Drawing, wherein like numerals denote like parts in both Figures, detection device 10 of FIG. 1 includes three monochromatic infrared light sources 11, 12 and 13, which can beam essentially a single wavelength of infrared light through a transparent window 25 and into a multiple internal reflection (MIR) crystal 15. In the embodiment of the detection device shown in FIG. 1, only one of the three infrared energy sources is in use, i.e. source 11, but the three sources 11, 12 and 13 can be used either simultaneously or seriatim, as desired. Another characteristic of the device shown in FIG. 1 is that dry, immobilized enzyme (e.g. AChE or BuChE), has been formed into an immobilized dry layer 17 on a surface of MIR crystal 15. Thus, layer 17 is an element of the device of FIG. 1. If layer 17 becomes unduly "aged" or degraded, it can be replaced with a new layer. (In a dosimeter reader of this invention, the dry enzyme would not be a element of the device but would be instead an element of, for example, a dosimeter badge, not shown, which can be pressed against an MIR crystal.) Absent the enzyme layer 17, the beam 31 from energy source 11 would simply pass through crystal 15 with little or no absorption taking place, and the beam as it exits from the crystal and passes through transparent window 25 would be of approximately the same intensity as the beam entering the crystal. But the enzyme layer 17, after multiple internal reflection, absorbs at least some infrared energy resulting in a more atenuated beam 33 exiting from sample compartment 21 and being measured for percent absorption in spectrophotometric measurement means 35.

Sample compartment 21 is provided with an air pump 19, so that the flow of air over enzyme layer 17 will be voluminous in a given period of time, say, eight hours. The air flow exits through exit port 29.

The device shown in FIG. 1 has both a detection and identification capability. The monochromatic energy sources 11, 12 and 13 provide coherent beams of energy of, for example, 750, 950, and 1650 cm$^{-1}$. Computer 37 has stored in its memory the percent absorption for a suitable enzyme (e.g. a cholinesterase) at 1650 cm$^{-1}$, a peak in the infrared spectrum of the enzyme which does not change, even if the enzyme has complexed with a nerve agent or an organophosphorus compound. Accordingly, the computer 37 can compare the output of the spectrophotometric measuring means 35 (shown in the Figure to be measuring the percent absorption of beam 31 having a wavelength of, for example, 750 cm$^{-1}$) with the 1650 cm$^{-1}$ peak stored in its memory and determine whether or not there has been any change in percent absorption at the wave length of beam 31, using the stored information as a type of baseline. The output 39 from the computer 37 can be, for example, a digital readout which can be understood by the trained operator of device 10. Typically, the operator can thereby learn not only of the existence of the agent in the air sample but also of the identity of the agent. If there is the possibility of more than one agent producing the readout observed by the operator, a second wavelength provided by monochromatic energy source 12 can be consulted for further identification purposes. Alternatively, output 39 from computer 37 can simply operate an alarm when the transmission of beam 31 through crystal 15 falls below a certain level.

Figure 2:
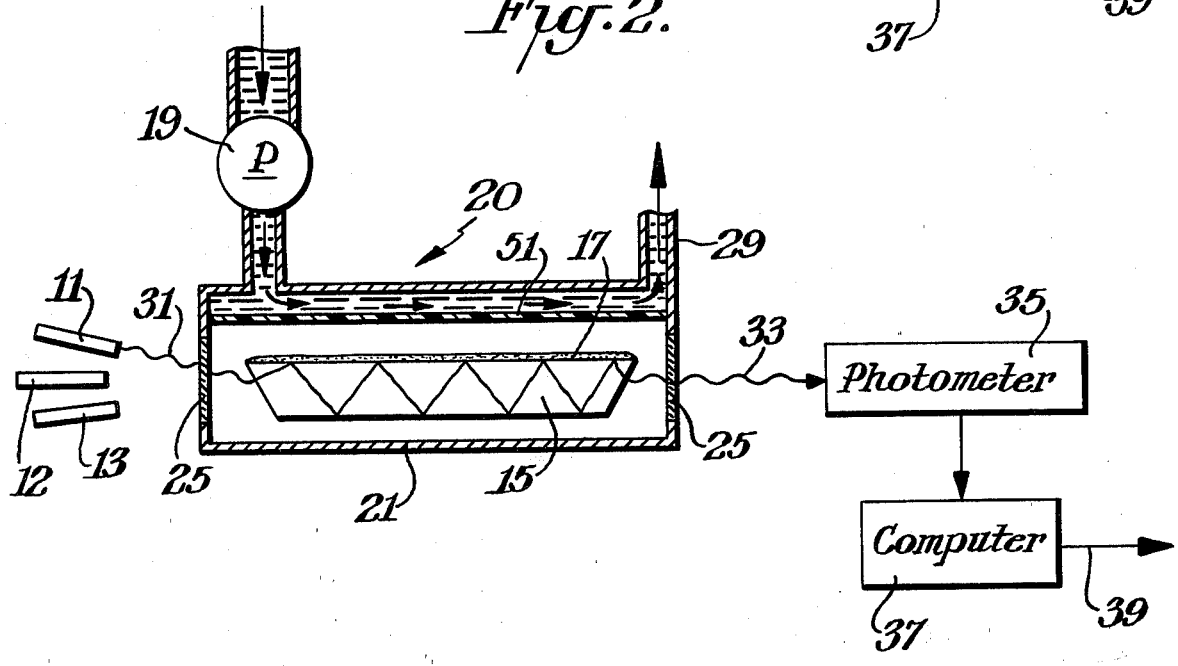
FIG. 2 is a modified form of the device of FIG. 1 with means to permit analysis of liquid samples.

The device shown in FIG. 2 works in a manner exactly analogous to the device of FIG. 1 except that means have been provided to analyze liquid samples. The liquid sample is pumped through the upper portion of sample compartment 21 and out through exit port 29 much as in the device of FIG. 1, except that a selectively permeable membrane 51 has been provided to permit the agent to pass through membrane 51 and complex with enzyme layer 17 without permitting any significant amount of water to create problems for the infrared analysis. Thus the beam 31 impinging upon crystal 15 would not penetrate to the water flow and would be relatively uneffected by moisture present in the system.

In both FIGS. 1 and 2, the reference peak stored in the memory of computer 37 is a quantified portion of a model spectrum (hence a model percent transmission) of a model sample of the type of enzyme used in layer 17, the model portion of the spectrum having been measured under conditions substantially identical to the conditions under which devices 10 and 20 operate, and in a more complicated version of the devices 10 and 20 (not shown in the Drawing), the entire spectrum of layer 17 can be analyzed and compared to a complete model spectrum or curve stored in the memory of computer 37. In any event, the operation of devices 10 and 20 is premised upon the computer storage of a model percent transmission of a model sample of the enzyme in an uncomplexed state, which model percent transmission was measured under the aforementioned conditions.

What is claimed is:

1. A method for detecting the presence in a fluid medium of an inhibitor capable of combining with an enzyme, comprising the steps of:
   (a) collecting a sample of said inhibitor in said fluid medium by bringing said fluid medium into contact with substantially uncombined enzyme, thereby forming an enzyme-inhibitor combination; and
   (b) detecting any infrared wave-energy interaction characteristic of said enzyme-inhibitor combination, which differs, at a given infrared wavelength, from the infrared wave-energy interaction characteristic of the substantially uncombined enzyme at said wavelength, said detecting step including the measurement of the percent transmission of infrared energy of the enzyme-inhibitor combination at the given wavelength, the percent transmission of infrared energy of the substantially uncombined enzyme at said wavelength being known.

2. A method according to claim 1 wherein said step (b) includes a comparison of the measurement of percent transmission of infrared energy of the enzyme-inhibitor combination at the given wavelength with the known percent transmission of infrared energy of the substantially uncombined enzyme at said wavelength.

3. A method according to claim 1 wherein both the percent transmission of an enzyme-inhibitor combination and the percent transmission of the substantially uncombined enzyme have been measured with model infrared transmission studies prior to commencing step (a) of the method.

4. A method according to claim 1 wherein said fluid medium is air.

5. A method according to claim 1 wherein said fluid medium is water.

6. A method according to claim 1 wherein the substantially uncombined enzyme is an immobilized state.

7. A method according to claim 1 wherein the detecting of any wave-energy interaction characteristics in step (b) includes the use of multiple internal reflection infrared spectroscopy.

8. A method according to claim 1 including the further step of annunciating the results of the comparison of said step (b).

9. A method according to claim 1 wherein said inhibitor is an anticholinesterase.

* * * * *